United States Patent [19]
Sheriff

[11] Patent Number: 5,891,726
[45] Date of Patent: Apr. 6, 1999

[54] PROCEDURE TO INCREASE THE SEED PRODUCTIVITY OF PLANTS AND TO ACCELERATE THE GROWTH OF PLANTS BY MEANS OF AN ADDITIONAL PLASTIDIC PYRUVATE, PHOSPHATE DIKINASE

[76] Inventor: Ahmed Sheriff, Geibelstrasse 1, D-12305 Berlin, Germany

[21] Appl. No.: 705,900

[22] Filed: Aug. 28, 1996

[30] Foreign Application Priority Data

Aug. 29, 1995 [DE] Germany .................. 195 31 783.1

[51] Int. Cl.⁶ .................. A01H 4/00; C07H 21/04; C07K 14/415; C12N 5/14
[52] U.S. Cl. .................. 435/419; 435/172.3; 530/370; 536/23.6; 800/278; 800/290; 800/298
[58] Field of Search .................. 435/172.3, 419; 530/370; 536/23.6; 800/278, 290, 298

[56] References Cited

U.S. PATENT DOCUMENTS

| | | |
|---|---|---|
| 4,970,160 | 11/1990 | Katsuki . |
| 5,387,756 | 2/1995 | Burrell et al. . |
| 5,510,471 | 4/1996 | Lebrun et al. . |

FOREIGN PATENT DOCUMENTS

| | | |
|---|---|---|
| 19531678 | 3/1997 | Germany . |
| 7184657 | 7/1995 | Japan . |
| WO 9515385 | 8/1995 | WIPO . |

OTHER PUBLICATIONS

Mutsuoka et al. PNAS USA, vol. 90, No. 20, Oct. 1993, pp. 9586–9590.

Fisslthaler et al. Planta, vol. 196, No. 3, Jul. 1995, pp. 492–500.

*Primary Examiner*—Jeffrey Stucker
*Assistant Examiner*—Phuong T Bui
*Attorney, Agent, or Firm*—Richard F. Trecartin; Flehr Hohbach Test Albritton & Herbert LLP

[57] ABSTRACT

The present invention includes novel methods for increasing the seed productivity or accelerating the growth rate of a plant and plants produced by such methods. Such plants have at least one cell transformed with an expression complex comprising a promoter operably linked to a gene encoding a pyruvate phosphate dikinase which is capable of converting pyruvate into phosphoenolpyruvate. The plants are made by transforming at least one plant cell with an appropriate expression construct, regenerating plants from one or more transformed plant cells and selecting at least one plant having the desired phenotype.

7 Claims, 8 Drawing Sheets

PPDK: pyruvate, phosphate dikinase
PEPCase: phospho*enol*pyruvate carboxylase

FIG._1

PPDK: pyruvate, phosphate dikinase
PEPCase: phospho*enol*pyruvate carboxylase
ME: malic enzyme
MDH: malate dehydrogenase

PROCEDURE TO INCREASE THE SEED PRODUCTIVITY OF PLANTS AND TO ACCELERATE THE GROWTH OF PLANTS BY MEANS OF AN ADDITIONAL PLASTIDIC PYRUVATE, PHOSPHATE DIKINASE

BACKGROUND OF THE INVENTION

Problem

Remarkable improvements in the yield and quality of cereal grains have been attained during the twentieth century by plant breeding and selection (Borlaug and Dowswell 1988). Nevertheless, such increases can not be sustained indefinitely. Of the many serious problems confronting humans, the most urgent is that of population growth. At the current rate of growth, world population is expected to double to 11 billion by the year 2030. This is already causing the loss of some of the best crop lands. To feed the world's population in 40 years' time, will require all our ingenuity. There is, therefore, an urgent need to increase food production by supplementing and complementing the traditional methods of plant improvement by the novel technologies of plant cell and molecular biology. These permit access to an unlimited gene pool by allowing the transfer of desirable genes between any two species of interest.

Plants are remarkable organisms. They are able to satisfy their energetical needs by means of the sunlight. In addition, they generate, by a process known as photosynthesis, carbohydrates from carbon dioxide. These substances can be used as energy stores, for biosynthesis as well as structural components. But, not all plant tissues are able to perform photosynthesis. All tissues which have no contact to light are non-photosynthetic (roots). Some tissues simply have other functions (developing seeds, vascular tissue). Naturally, photosynthesis can not be performed in the dark. During the light phase, photosynthetically active tissues must produce and store enough energy to supply the whole organism and if possible, to drive growth and reproduction. Usually, sugars are the means of short term storage (starch, sucrose) and transfer (sucrose) of energy. The main sinks for sucrose are developing leaves and non-photosynthetically active tissues. The non-photosynthetically active plant tissues must generate their complete organic components from the transferred carbon scaffolds (Dennis and Turpin 1990; Mohr and Schopfer 1978; Strasburger et al. 1991; Taiz and Zeiger 1991).

Respiration of the hexoses glucose and fructose derived from sucrose can generate up to 38 ATP* (Voet and Voet 1992). Simultaneously, carbon dioxide assimilated during

*Adenosine triphophate (ATP) is the energy currency of the cell. The change of free energy ($\Delta G$) for ATP hydrolysis is under physiological circumstances −50 to −65 kJ/mol. One NADH can be converted to 3 ATP. photosynthesis will be set free again. Photosynthesis needs 18 ATP and 12 NADPH to produce one hexose molecule (Mohr and Schopfer 1978; Strasburger et al. 1991; Taiz and Zeiger 1991). This equals an energy amount of 54 ATP. A simple calculation shows that 16 ATP are lost from photosynthesis to respiration.

Can respiration reduce crop yield? The answer is: Yes. A 20% reduction of respiration can lead to 10–20% increased crop productivity (Lambers 1985; Wilson and Jones 1982). Unluckily, in the field, one can not easily prolong light periods or optimize growth temperatures, air- and soil humidity. Therefore, other solutions to reduce loss of carbon dioxide by respiration must be developed.

BRIEF SUMMARY OF THE INVENTION

Possible Solution

Figure 1:
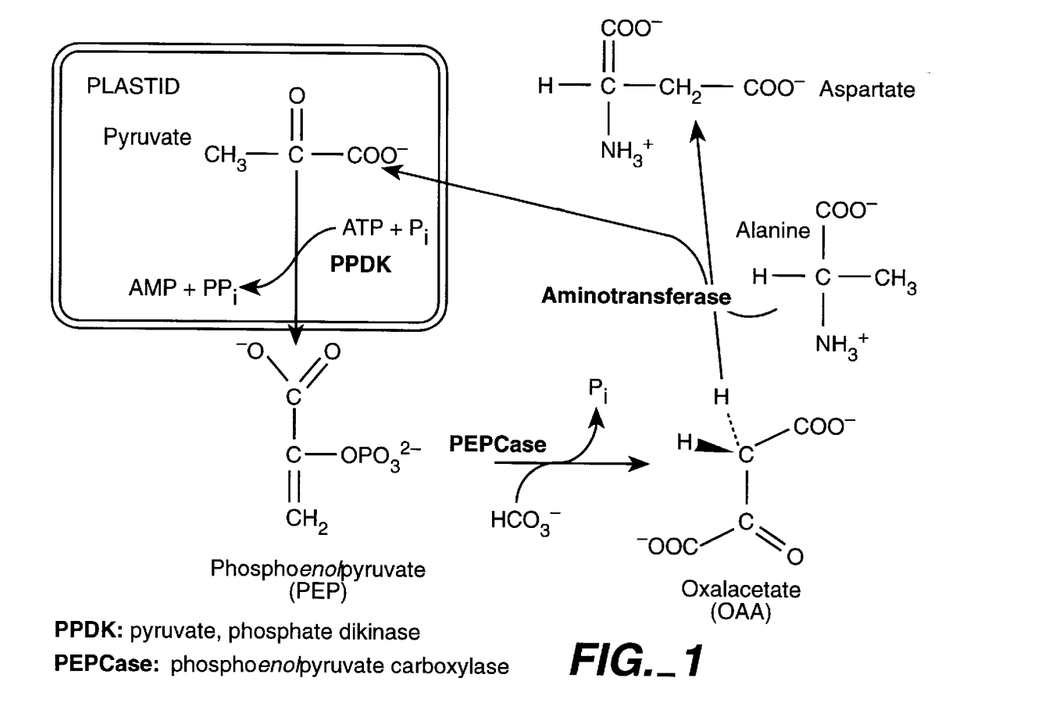
FIG. 1: The metabolic scheme according to Latzko and Kelly (1983) shows a possibility to refix respiratory $CO_2$ and produce oxaloacetate as a precursor for amino acid biosynthesis.

Is there a possibility to refix carbon dioxide which was set free during respiration, independent of photosynthesis? A biochemical possibility to refix carbon dioxide is shown in FIG. 1 (Latzko and Kelly 1983). This fixation is catalysed by phosphoenolpyruvate carboxylase (PEPCase; EC 4.1.1.31). PEPCase is a key enzyme of the anaplerotic metabolism (supplying the tricarboxylic acid cycle with substrates). Plant pyruvate, phosphate dikinase (PPDK; EC 2.7.9.1) is a plastidic enzyme which is assumed to produce phosphoenolpyruvate (PEP) for the PEPCase reaction in non-photosynthetically active tissues (Latzko and Kelly 1983; Meyer et al. 1978).

The product of phosphoenolpyruvate carboxylation is oxaloacetate which can be converted to aspartic acid by a transaminase reaction. Alanine could serve as a substrate. Alanine on the other hand is converted to pyruvate, which again can be a substrate for PPDK. The cycle shown in FIG. 1 demonstrates that carbon dioxide can be assimilated at the expense of two energy rich phosphate moieties (equivalent to two ATP). The Calvin cycle needs three ATP and two $NADPH+H^+$ (equivalent to nine ATP) for the assimilation of one carbon dioxide (Taiz and Zeiger 1991). The refixation of carbon dioxide by PPDK and PEPCase could help plants to save lots of energy (seven ATP per refixed carbon dioxide) and reuses part of the carbon dioxide set free by respiration.

Figure 2:
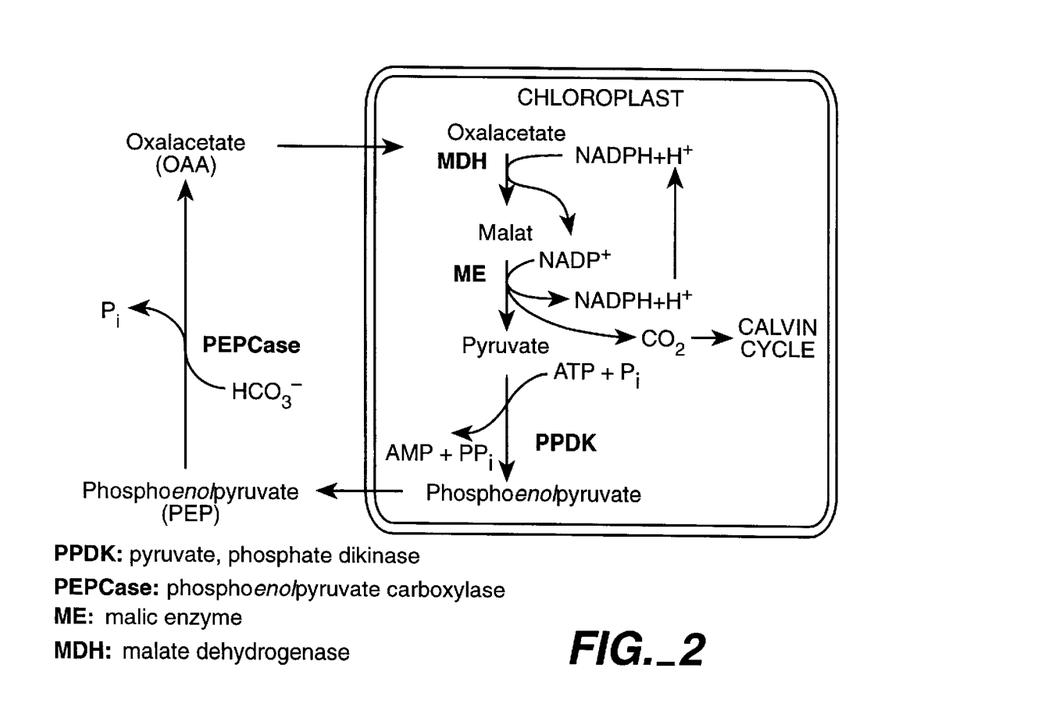
FIG. 2: The metabolic scheme according to Aoyagi und Bassham (1986) shows a possibility to enrich $CO_2$ intracellularly.

Another reason for the occurrence of PEPCase and PPDK in photosynthetically active tissues of $C_3$ plants was suggested by Aoyagi and Bassham (1986; Abbildung 2). Here, PEPCase and PPDK are supposed to enrich carbon dioxide intracellularly, which could lead to increased carbon dioxide fixation by ribulose-1,5-bisphosphate carboxylase (RubisCo). This way of primary carbon dioxide fixation and enrichment is utilized by CAM and $C_4$ plants. But, in CAM plants PEPCase (night) and RubisCo (day) are active at different times of the day, while in $C_4$ plants PEPCase (mesophyll cells) and RubisCo (bundel sheath cells) are spatially divided because both enzymes are competing for the same substrate (Dennis and Turpin 1990; Mohr and Schopfer 1978; Strasburger et al. 1991; Taiz and Zeiger 1991; Ting 1985).

Latzko and Kelly (1983) suggested another ten biochemical reason for the occurrence of PEPCase. But, these other purposes do not bring about immediate energetical advantages. Phosphoenolpyruvate is a substrate for PEPCase. It can, for example, be generated from pyruvate by PPDK and, maybe PEPCase is limited by the supply of phosphoenolpyruvate. The enzymatic characteristics and metabolic functions of PPDK from non-photosynthetically active tissues are only poorly understood (Fißlthaler et al. 1995; Rosche et al. 1994).

My idea was, to remedy a possible shortage of phosphoenolpyruvate. My main assumption is that PPDK is the limiting factor. When plants are forced to produce increased amounts of PPDK, such a shortage might be overcome. To proof this idea, I expressed a cDNA for the plastidic enzyme derived from the facultative CAM plant *Mesembryanthemum crystallinum* (Fißlthaler et al. 1995) in the $C_3$ plant tobacco [*Nicotiana tabacum* (Samsun SNN)]. The test system tobacco only serves as a model and was chosen because it can easily be manipulated. The PPDK from *M. crystallinum* serves as a representative of this enzyme class and was chosen because of its availability.

BRIEF DESCRIPTION OF THE DRAWINGS

FIG. 3: Schematic drawing of the binary vectors with the M. crystallinum PPDK-insertion. Δ represents a deletion of 183 bp at the 5'-end. The PPDK cDNA-sequence from M. crystallinum is 3173 bp long (Fißlthaler et al. 1995). The transnational start-codon is at position 63. The termination codon is at position 1920. The protein deduced from the cDNA sequence contains 949 amino acids (aa), which corresponds to a relative molecular mass ($M_r$) of 103244 daltons. The presequence has a length of 74 aa. The mature plastidic enzyme has a $M_r$ of 94 kDa. 5'- and 3'-untranslated parts of the cDNA are indicated as terminal hatched boxes (left 5'-, right 3'-untranslated region; the dotted box represents the plastid presequence with three ATGs in the open reading frame). The T-DNA contained a neomycin phosphotransferase (nptll, kanamycin resistance) with plant regulatory elements. 35S CaMV: promoter of the cauliflower mosaic virus; ocs polyA: polyadenylation signal of the octopin synthase gene from A. tumefaciens; BR, BL: right, left borders of the T-DNA of Agrobacterium tumefaciens; Km: kanamycin resistance with prokaryotic regulational elements (Beven 1984). Transformation of the tobacco plants by A. tumefaciens was performed according to Horsch et al. (1985).

FIG. 9: Composition of seeds from the PPDK-overexpressing tobacco lines with respect to weight and protein, sugar and lipid content. The amounts of protein, sugar and lipid are calculated per weight of one seed of the respective plant line. for the determination of the seed weight 6×100 wildtype seeds, 3×100 seeds of five of the PPDK-overexpressing tobacco lines were weighed. Protein content of the wildtype and of all of the transformands seeds were determined. Shown are only values of seeds which weight was determined. All other transformands seeds accumulated the same protein amounts within the measuring accuracy. Standard errors are indicated. No significant changes were detected (t-test, P>0.1). The protein content was determined with Coomassie blue (Spector 1978). The sugar analysis was performed as described (Carroll et al. 1956) and detects sugars only in the form of monosaccharides. The lipid analysis was performed with 100 mg of seeds as described (Zöllner and Kirsch 1962). Sunflower oil was used as standard.

DETAILED DESCRIPTION OF THE INVENTION

Solutions

Figure 3:
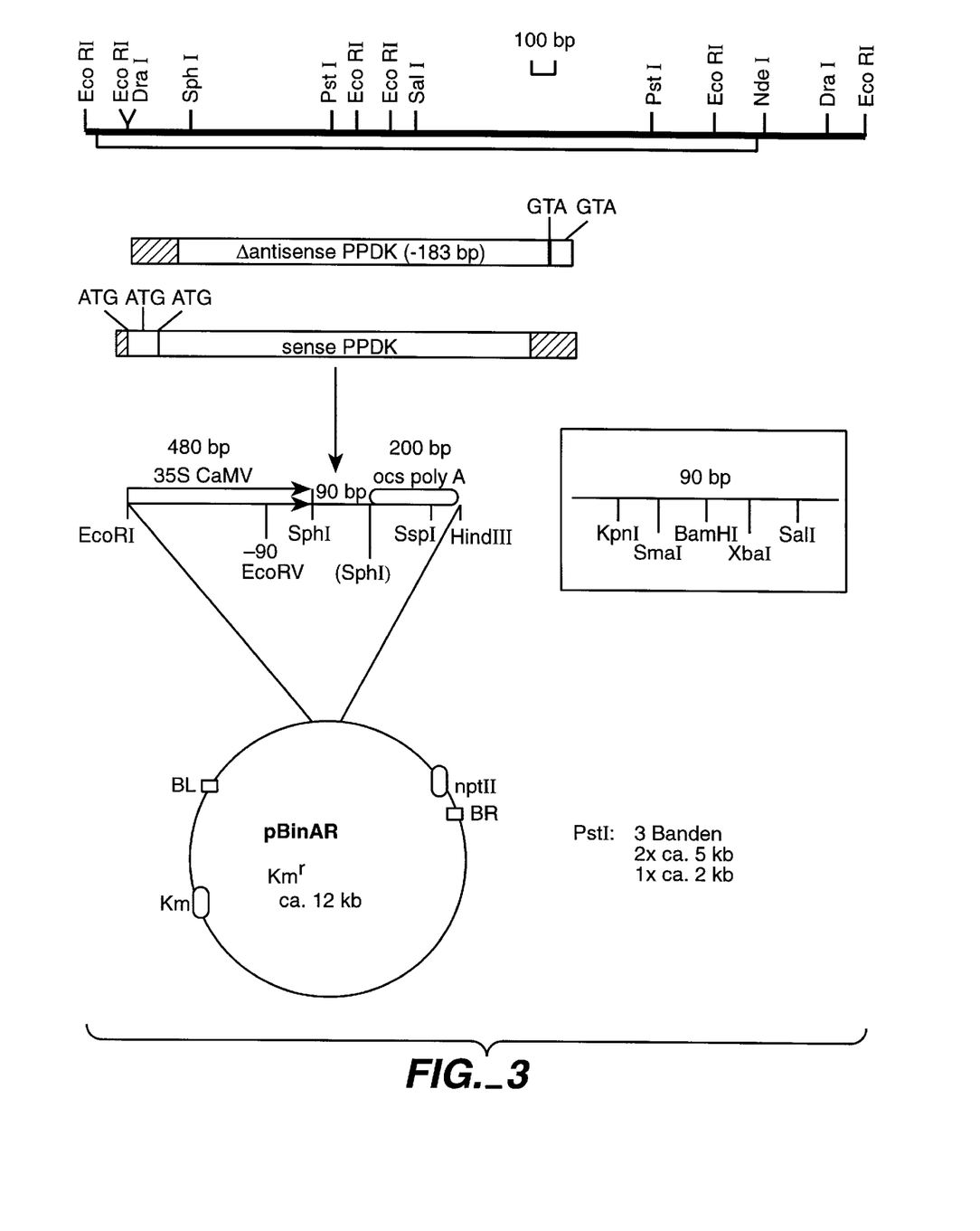

The cDNA specific for the M. crystallinum PPDK encodes a precursor polypeptide of 103 kDa processed to a 94 kDa plastidic enzyme (Fißlthaler 1993; Fißlthaler et al. 1995). This cDNA was introduced into a binary expression-vector (Bevan 1984; FIG. 3). A control construct contains this cDNA in reversed orientation (Δantisense). This reversed cDNA lacked 183 base pairs at its former 5'-end. Both ppdk cDNAs were under control of the constitutive CaMV 35S-promoter. As a control the same vector containing β-glucuronidase (Vancanneyt et al. 1990) instead of ppdk was used. The constructs were transferred by Agrobacterium tumefaciens to a random location of the plant genome. Therefore, individual transformands are expected to vary in the degree of expression (Schell 1987). The control constructs (Δantisense-PPDK and β-glucoronidase) were in all experiments very similar to the wildtype. Further on, they will not always be mentioned.

Figure 4:
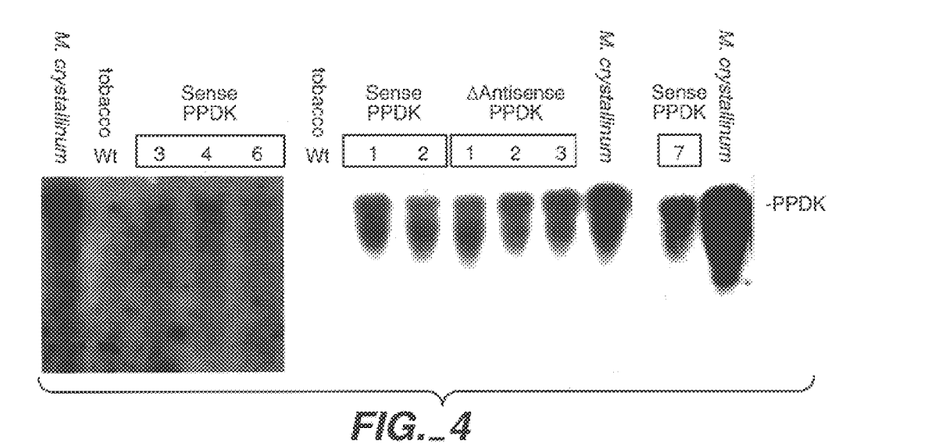
FIG. 4: Northern blots of ppdk and Δppdk mRNA from leaves of PPDK- and ΔPPDK-overexpressing tobacco plants. Leaf RNA of the wildtype (Wt) served as a negative control and leaf RNA of a CAM performing M. crystallinum served as a positive control. The individual PPDK transformands have the same numbers in all figures. 40 μg tobacco RNA and 20 μg M. crystallinum RNA were loaded.
Figure 5:
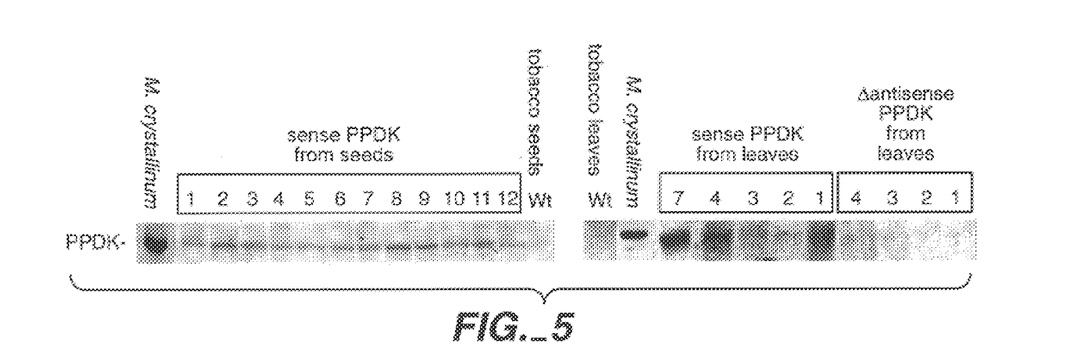
FIG. 5: Western blots of PPDK-overexpressing tobacco plants to monitor the PPDK protein level. Two μg crude extract of a salt-stressed M. crystallinum served as a positive control. Wildtype (Wt) plants and Δantisense-tobacco plants served as negative controls. Sixty-two μg of the soluble leaf proteins and 45 μg of the soluble seed proteins of the tobacco plants were applied. The analysed transgenic plants were from the F1-generation of independent transformands.

The heterologous PPDK and ΔPPDK genes were transcribed in tobacco leaves (FIG. 4). Sense- as well as Δantisense mRNA was detected. In comparison to the mRNA level of PPDK in CAM-performing leaves of M. crystallinum, the mRNA level of the heterologous PPDK in the transformands was about 25%. No ppdk mRNA-signal could be obtained from the tobacco wildtype under the hybridization conditions used. PPDK protein could be detected in seeds as well as leaves of PPDK plants (FIG. 5). However, the protein amount of PPDK was much lower than expected on the basis of the Northern analysis (FIG. 1B). In the wildtype or Δantisense plants, no or only minor PPDK amounts could be detected.

Figure 6:
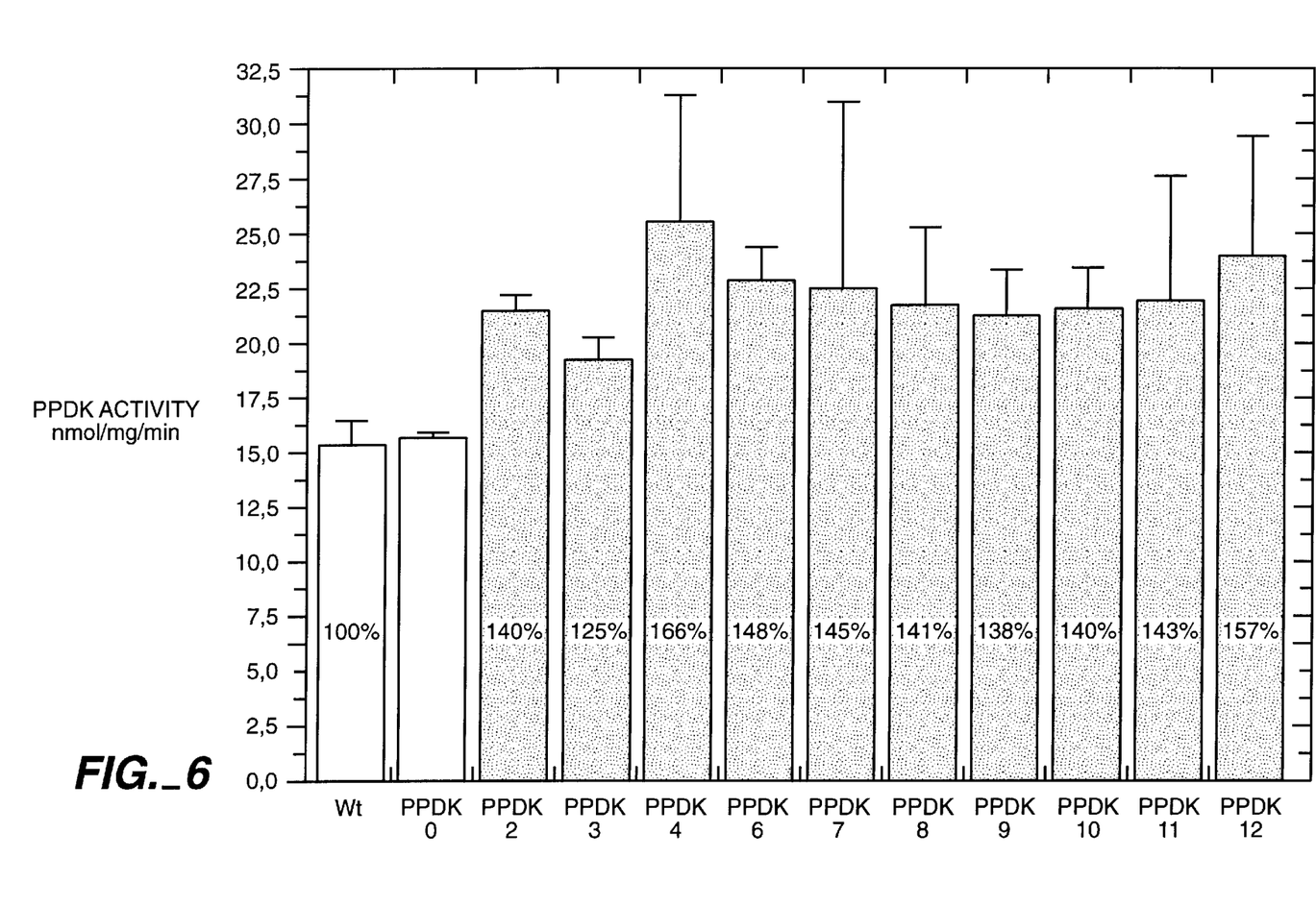
FIG. 6: PPDK activity in leaves. PPDK was extracted and measured as described (Holtum and Winter 1982) but without pyruvate and $KH_2PO_4$ in the homogenization buffer. PPDK activity was determined from crude leaf extracts of the wildtype (Wt), the control transformand containing a β-glucuronidase gene (Gus), and tobacco lines with additional M. crystallinum PPDK. The standard errors of ten (Gus, PPDK2–4 and PPDK7–12), 28 (PPDK6) and 41 (Wt) independent measurements are shown. Changes in PPDK activity are significant (t-test, P<0.05, with the exception of PPDK8: P<0.1).

FIG. 6 shows that the PPDK-overexpressing tobacco plants had higher PPDK activities as well (PPDK: 125–166% of the wildtype activity). As expected, the degree of PPDK activity varied between individual transgenic plants. The β-glucuronidase control-transformand did not show increased PPDK activity. The PPDK activity of the wildtype was in the same range as reported by others (Edwards et al. 1980; Kisaki et al. 1973).

The evaluation of the productivity of the PPDK-overexpressing tobacco lines revealed that these plants grew faster (FIG. 7) and produced seeds about three weeks earlier than the wildtype.

The data in FIG. 8 demonstrate the effect of the additional PPDK on seed production. Strikingly, all eleven lines analysed produced more seeds per seed capsule than the wildtype (=100%). Line PPDK 6 reached the highest value with 174%. This increase in productivity coincided with an increase in the ratio of the weights of seeds per seed capsule. While the wildtype seeds made up 50% of the weight of the seed capsule, the seeds of the PPDK-overexpressing plants made up about 65% of the weight of the seed capsule. In this respect, the most effective line was PPDK 2 with 77%. In addition, the weight of the seed capsule itself was higher for most of the PPDK-overexpressing tobacco lines than for the wildtype. Line PPDK 6 peaked here with 125%. Consistently, most of these lines produced more seeds altogether, too. PPDK 2 was the highest with 185%. Taken together, PPDK-overexpressing plants did not produce more seed capsules than the wildtype, but more seeds per seed capsule (up to 74% more).

The seeds produced by the PPDK-overexpressing tobacco were 90% germinable, similar to the wildtype. Tobacco seeds store mainly lipids (about 48% of the seed weight), sugars and protein but no starch. No significant alterations were detected with regard to weight or composition of seeds of the PPDK-overexpressing plants (FIG. 9). Tobacco seeds accumulate no starch but soluble sugars. The main storage compound were lipids (48% of the seed weight). Free sugars and proteins made up only 8% of the seed weight.

Conclusions

Figure 7:
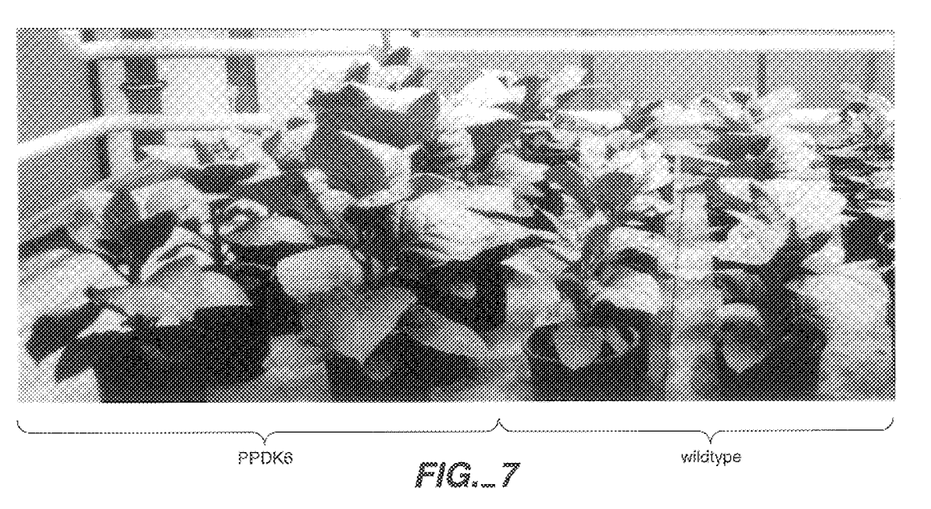
FIG. 7: Difference of growth rate of wildtype (right) and a PPDK-overexpressing tobacco line (PPDK6) four month after sowing. One transgenic line is shown exemplarily.
Figure 8A:
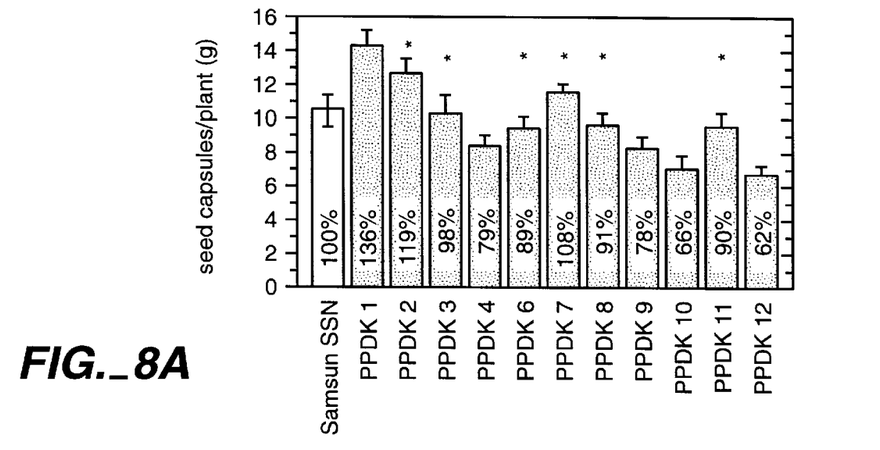
FIG. 8: Seed productivity of PPDK-overexpressing tobacco lines. For the analysis 33 wildtype plants and 155 of the PPDK-overexpressing tobacco plants were grown to see maturity. The following numbers of individual independent transformands (F1-generation) were analysed: PPDK transformand Nr. 6: 16 plants; PPDK transformand Nr. 1, 2, 8, 9, 12: 15 plants each; PPDK transformand Nr. 4: 14 plants; PPDK transformand Nr. 3, 10: 13 plants each; PPDK transformand Nr. 7, 11: 12 plants each. The standard errors are indicated. Non-significant changes are indicated by an asterisk (*; t-test, P>0.1). All others are significant (t-test, P<0.05).
Figure 8B:
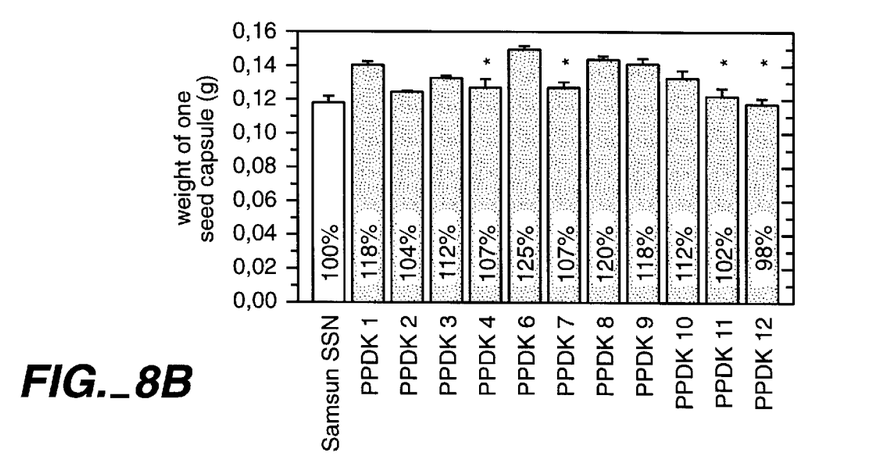
Figure 8C:
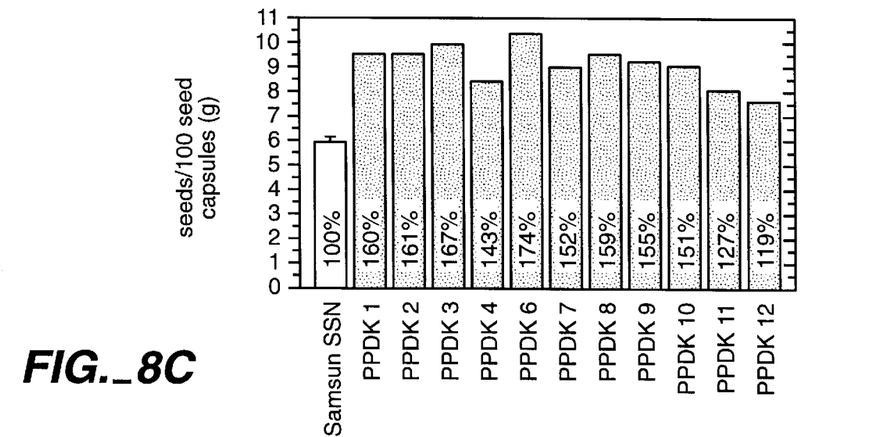
Figure 8D:
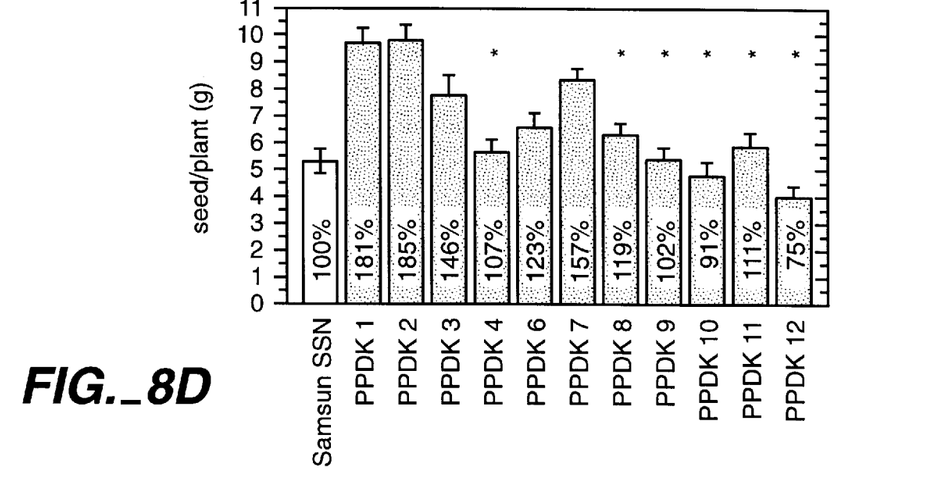
Figure 8E:
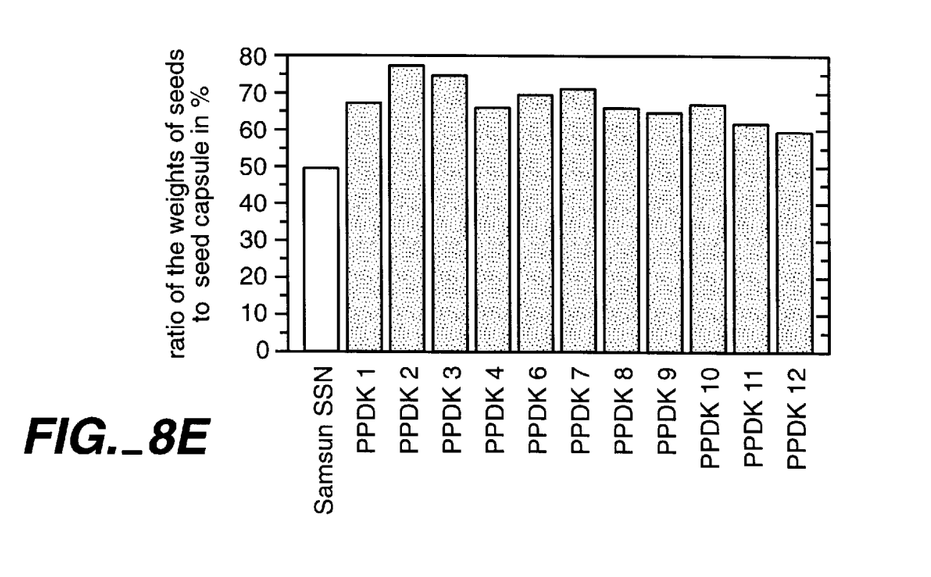
Figure 9A:
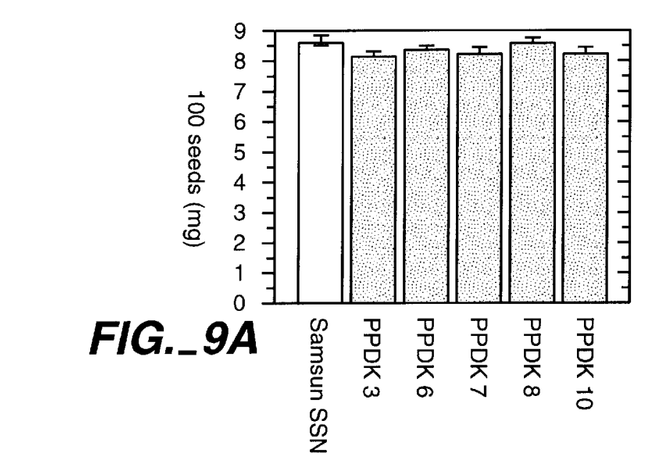
Figure 9B:
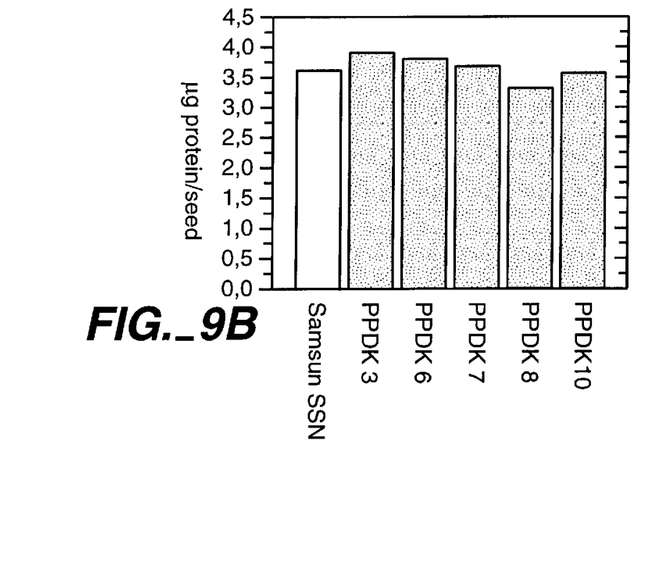
Figure 9C:
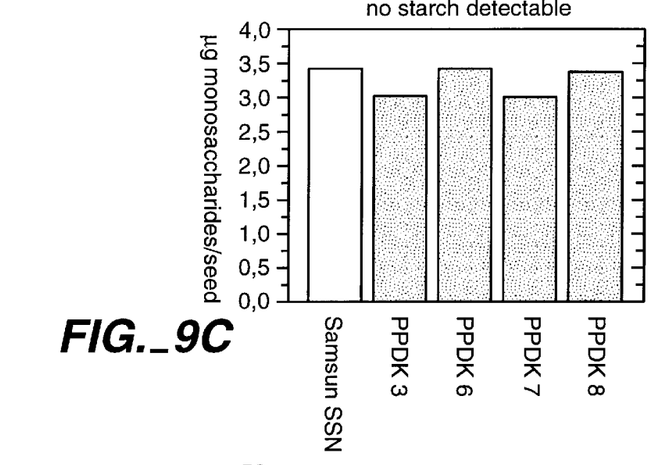
Figure 9D:
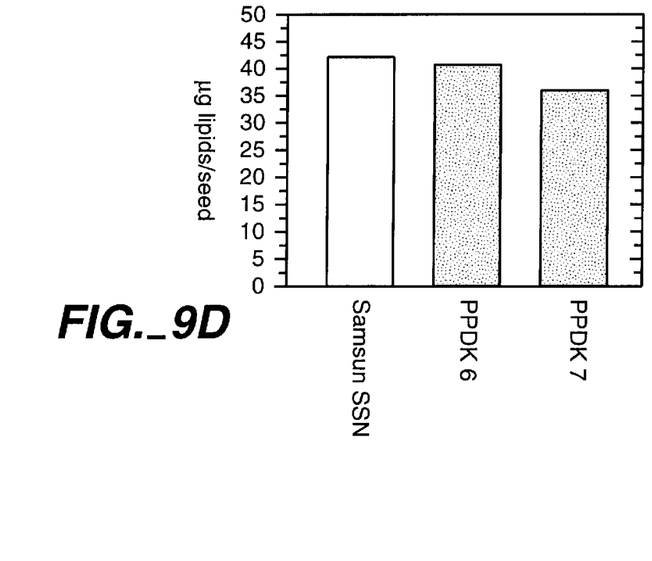

The following conclusions can be drawn from the data: Plants with additional plastidic PPDK grow faster. These plants produce more seeds than the wildtype. The increased seed productivity was due to heavier seed capsules and more seeds per seed capsule. The physiological basis of the increased growth rate and productivity of the PPDK-overexpressing tobacco is poorly understood at present, but is most likely due to refixation of carbon dioxide (see FIG. 1) produced by respiration. The additional plastidic PPDK produces the PEPCase and refixation substrate phosphoenolpyruvate in increased amounts and so, remedies a energy waste and carbon loss bottle-neck. Even the slightest measured increase in activity (125%) initiated increased seed productivity and faster growth rates of the transformands (FIG. 6, 7 and 8).

The strong effects of PPDK on the growth rate and productivity of tobacco described here suggest that photosynthetic carbon assimilation is not limiting to growth and yield. It is surprising that a single enzymatic step can have such a dramatic effect on desirable traits in an agriculturally important plant. Genetic engineering with a plastidic PPDK to produce additional PEP should also improve other plants in the parameters described above.

Referenzen

Aoyagi K. and Bassham J. A. (1986) Appearance and accumulation of $C_4$ carbon pathway enzymes in developing wheat leaves. *Plant Physiol.* 80, 334–340.

Bevan M. (1984) Binary Agrobacterium vectors for plant transformation. *Nucl. Acids Res.* 12, 8711–8721.

Borlaug N. E. and Dowswell C. R. (1988) World revolution in agriculture. In *Book of the Year* 1988, eds) Chicago: Encyclopedia Britannica, pp. pp. 514.

Carroll N. V., Langley R. W. and Roe J. H. (1956) The determination of glycogen in liver and muscle by use of anthrone reagent. *J. Biol. Chem.* 220, 583–593.

Dennis D. T. and Turpin D. H. (1990) Plant Physiology, Biochemistry and Molecular Biology. Longman Group UK Limited, Essex Edwards G. E., Ujihira M. and Sugiyama T. (1980) Light and temperature dependence of the rate and degree of activation of pyruvate, $P_i$ dikinase in vivo in maize. *Photosynth. Res.* 1, 199–207.

Fißlthaler B. (1993) Die Pyruvat, Phosphat Dikinase aus der fakultativen Crassulaceen-Säurestoffwechsel-Pflanze *Mesembryanthemum crystallinum*: Sequenzierung und Charakterisierung des Gens. Freie Universität Berlin, Dissertation Fisslthaler B., Meyer G., Bohnert H. J. and Schmitt J. M. (1995) Age-dependent induction of pyruvate, othophosphate dikinase in *Mesembryanthemum crystallinum L. Planta* 196, 492–500.

Horsch R. B., Fry J. E., Hoffmann N. L., Eichholtz D., Rogers S. G. and Fraley R. T. (1985) A simple general method for transferring genes into plants. *Science* 227, 1229–1231.

Kisaki T., Hirabayashi S. and Yano N. (1973) Effect of the age of tobacco leaves on photosynthesis and photorespiration. *Plant Cell Physiol.* 14, 505–514.

Lambers H. (1985) Respiration in intact plants and tissues. Its regulation and dependence on environmental factors, metabolism and invaded organisms. In *Higher Plant Cell Respiration*, (Douce R. and Day D. A., eds) Berlin: Springer-Verlag, pp. 418–473.

Latzko E. and Kelly G. J. (1983) The many-faceted function of phosphoenolpyruvate carboxylase in $C_3$ plants. *Physiol. Veg.* 2, 805–815.

Meyer A. O., Kelly G. J. and Latzko E. (1978) Pyruvate orthophosphate dikinase of immature wheat grains. *Plant Sci. Lett.* 12, 35–40.

Mohr H. and Schopfer P. (1978) Lehrbuch der Pflanzenphysiologie. Springer-Verlag, Berlin Rosche E., Streubel M. and Westhoff P. (1994) Primary structure of the photosynthetic pyruvate orthophosphate dikinase of the $C_3$ plant *Flaveria pringlei* and expression analysis of pyruvate orthophosphate dikinase sequences in $C_3$, $C_3$–$C_4$ and $C_4$ Flaveria species. *Plant Mol. Biol.* 26, 763–769.

Schell J. (1987) Transgenic Plants as Tools to Study the Molecular Organization of Plant Genes. *Science* 237, 1176–1183.

Spector T. (1978) Refinement of the Coomassie blue method of protein quantitation. *Anal. Biochem.* 86, 142–146.

Strasburger E., Noll F., Schenck H. and Schimper A. F. W. (1991) Lehrbuch der Botanik. Gustav Fischer Verlag, Stuttgart Taiz L. and Zeiger E. (1991) Plant Physiology. The Benjamin/Cummings Publishing Company, Inc., Redwood City Ting I. P. (1985) Crassulacean acid metabolism. *Ann. Rev. Plant. Physiol.* 36, 595–622.

Vancanneyt G., Schmidt R., O'Connor-Sanchez A., Willmitzer L. and Rocha-Sosa M. (1990) Construction of an intron-containing marker gene: Splicing of the intron in transgenic plants and its use in monitoring early events in Agrobacterium-mediated plant transformation. *MGG* 220, 245–250.

Voet D. and Voet J. G. (1992) Biochemie. VCH, Weinheim

Wilson D. and Jones J. G. (1982) Effect of selection for dark respiration rate of mature leaves on crop yields of *Lolium perenne* cv. S23. *Ann. Bot.* 49, 313–320.

Zöllner N. and Kirsch K. (1962) Über die quantitative Bestimmung von Lipoiden (Mikromethode) mittels der vielen natürlichen Lipoiden (allen bekannten Plasmalipoiden) gemeinsamen Sulfophosphovanilin-Reaktion. *Z. ges. exp. Med.* 135, 545–561.

I claim:

1. A method for producing a plant having increased seed productivity or an accelerated growth rate, said method comprising the steps of
   a) transforming one or more plant cells with an expression complex comprising a promoter operably linked to a gene encoding a plastidic pyruvate phosphate dikinase, wherein said promoter is other than the promoter naturally occurring with said gene;
   b) regenerating plants from said one or more transformed plant cells; whereby said plant having increased seed productivity or accelerated growth rate is produced.

2. The method according to claim 1, wherein said gene encoding a plastidic pyruvate phosphate dikinase is from a facultative CAM plant.

3. The method according to claim 1, wherein said one or more plant cells are $C_3$ plant cells.

4. A plant comprising at least one plant cell comprising an expression complex comprising a promoter operably linked to a gene encoding a plastidic pyruvate phosphate dikinase, wherein said promoter is other than the promoter naturally occurring with said gene.

5. The plant according to claim 4, wherein said gene encoding a plastidic pyruvate phosphate dikinase is from a facultative CAM plant.

6. The plant according to claim 4, wherein said promoter comprises a cauliflower mosaic virus promoter.

7. The plant according to claim 4, wherein said plant is a $C_3$ plant.

* * * * *